United States Patent
Pachinger et al.

(10) Patent No.: US 9,404,885 B2
(45) Date of Patent: Aug. 2, 2016

(54) AMPEROMETRIC GAS SENSOR

(71) Applicant: E+E Elektronik Ges.m.b.H, Engerwitzdorf (AT)

(72) Inventors: Dietmar Pachinger, Scharten (AT); Ernst Zotl, Reid i. d. Riedmark (AT); Georg Niessner, Katsdorf (AT)

(73) Assignee: E+E ELEKTRONIK GES.M.B.H., Engerwitzdorf (AT)

( * ) Notice: Subject to any disclaimer, the term of this patent is extended or adjusted under 35 U.S.C. 154(b) by 217 days.

(21) Appl. No.: 14/259,247

(22) Filed: Apr. 23, 2014

(65) Prior Publication Data
US 2014/0326602 A1     Nov. 6, 2014

(30) Foreign Application Priority Data
May 2, 2013   (EP) .................................... 13166237

(51) Int. Cl.
*G01N 27/407*  (2006.01)

(52) U.S. Cl.
CPC ........ *G01N 27/4071* (2013.01); *G01N 27/4073* (2013.01)

(58) Field of Classification Search
CPC . G01M 15/10; G01M 15/102; G01M 15/104; G01N 1/2252; G01N 27/404–27/407; G01N 27/409; G01N 27/419; G01N 27/41; F01N 2560/00–2560/20; F01N 2550/00–2550/24; F01N 3/10; F01N 11/00
See application file for complete search history.

(56) References Cited

U.S. PATENT DOCUMENTS

| | | | |
|---|---|---|---|
| 5,820,745 A * | 10/1998 | Van Geloven | 205/789 |
| 6,174,421 B1 * | 1/2001 | Schumann | 204/424 |
| 2002/0046947 A1 * | 4/2002 | Lawless | 204/426 |
| 2003/0034246 A1 | 2/2003 | Liu et al. | |
| 2012/0055789 A1 * | 3/2012 | Swartz et al. | 204/415 |

FOREIGN PATENT DOCUMENTS

| | | |
|---|---|---|
| DE | 2304464 A1 | 8/1974 |
| DE | 4445033 A1 | 6/1996 |
| DE | 202004015400 U1 | 12/2004 |

OTHER PUBLICATIONS

Resistivity Chart (downloaded Jan. 20, 2016).*
Peng et al. (Sensors and Actuators B 72 (2001) 35-40).*
Yu et al. (Sensors and Actuators B, 2002, 212-218).*

* cited by examiner

*Primary Examiner* — Jennifer Dieterle
(74) *Attorney, Agent, or Firm* — Leydig, Voit & Mayer, Ltd.

(57) ABSTRACT

An amperometric gas sensor for determining oxygen content in a gas mixture includes a solid-state electrolyte. A first electrode configured as a cathode and a second electrode configured as an anode are disposed on the solid-state electrolyte and exposed to the gas mixture. The cathode is in contact with the gas mixture without any interposed diffusion barrier and has a design such that a flow of oxygen molecules from the gas mixture to a three-phase boundary between the solid-state electrolyte, the cathode and the gas mixture is limited in a defined manner. A voltage source configured to apply a DC voltage between the electrodes. A measuring device is configured to measure a limiting current flowing between the electrodes as a measure of the oxygen content in the gas mixture.

12 Claims, 3 Drawing Sheets

AMPEROMETRIC GAS SENSOR

CROSS-REFERENCE TO PRIOR APPLICATION

Priority is claimed to European Patent Application No. EP 13 166 237.1, filed on May 2, 2013, the entire disclosure of which is hereby incorporated by reference herein

FIELD

The present invention relates to an amperometric gas sensor which is suitable, in particular, for determining the oxygen content in gas mixtures.

BACKGROUND

From the prior art, it is known to determine the oxygen content in gas mixtures using amperometric gas sensors based on solid-state electrolytes. The solid-state electrolyte functions as a substrate and has arranged thereon electrodes in the form of a cathode and an anode between which a DC voltage can be applied by means of a voltage source. The gas mixture whose oxygen content is to be determined surrounds the two electrodes and the solid-state electrolyte. The electrodes, together with the solid-state electrolyte and the surrounding gas mixture, each form what is known as a "three-phase boundary." At the three-phase boundary of the cathode, the oxygen molecules are ionized and incorporated into vacancies in the lattice of the solid-state electrolyte. Application of a voltage causes a current to flow through the electrodes and the solid-state electrolyte. Charge transfer is via the vacancies in the lattice of the solid-state electrolyte. At the three-phase boundary of the anode, a reverse reaction takes place and the recombined oxygen molecules are released into the gas mixture.

In order to determine the oxygen concentration in the gas mixture, a so-called "limiting current behavior" of the current-voltage characteristic is needed because in the limiting current range, the absolute magnitude of the resulting current, on the one hand, is nearly independent of temperature and voltage and, on the other hand, is linearly dependent on the oxygen concentration in the gas mixture. The limiting current flowing between the electrodes upon application of a DC voltage is measured by a suitable measuring device, and thus provides a measure of the oxygen content of the gas mixture. In order to ensure a suitable limiting current behavior of the current-voltage characteristic, it is necessary to limit, by selective intervention, the current along the current path cathode—transition cathode/solid-state electrolyte—solid-state electrolyte—transition solid-state electrolyte/anode—anode. The measure commonly used for this purpose is to limit the flow of oxygen molecules to the cathode by means of a diffusion barrier. In this regard, reference is made, for example, to DE 20 2004 015 400 U1. In certain sensor designs, however, it is problematic to provide a sufficiently thick diffusion barrier of this kind because of the production technology used.

SUMMARY

In an embodiment, the present invention provides an amperometric gas sensor for determining oxygen content in a gas mixture including a solid-state electrolyte. A first electrode configured as a cathode and a second electrode configured as an anode are disposed on the solid-state electrolyte and exposed to the gas mixture. The cathode is in contact with the gas mixture without any interposed diffusion barrier and has a design such that a flow of oxygen molecules from the gas mixture to a three-phase boundary between the solid-state electrolyte, the cathode and the gas mixture is limited in a defined manner. A voltage source configured to apply a DC voltage between the electrodes. A measuring device is configured to measure a limiting current flowing between the electrodes as a measure of the oxygen content in the gas mixture.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
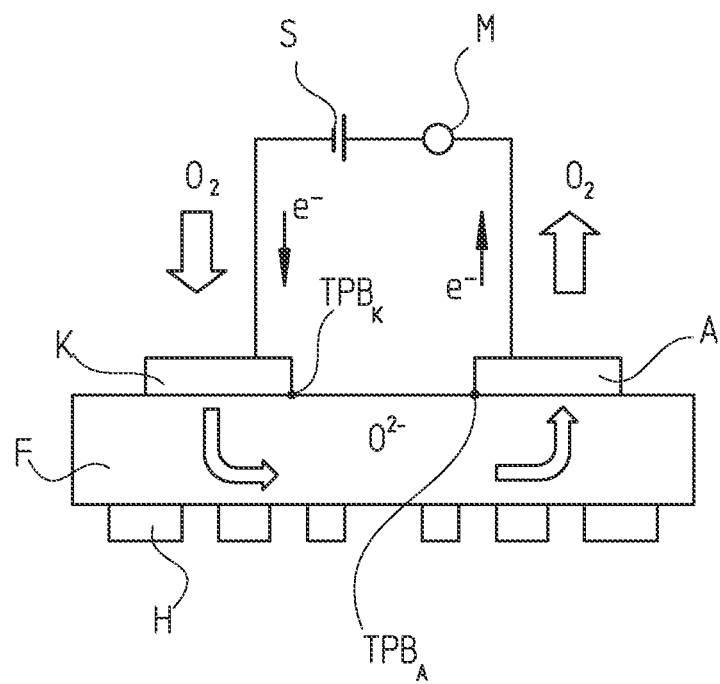
FIG. 1 is a schematic diagram of the gas sensor according to an embodiment of the present invention.

In an embodiment, the present invention provides an amperometric gas sensor for determining the oxygen content in gas mixtures that is based on the limiting current principle and can be operated without a separate diffusion barrier. The limiting current behavior of the gas sensor in the relevant temperature range in which the gas sensor is operated is advantageously as reproducible as possible.

The amperometric gas sensor according to an embodiment of the present invention for determining the oxygen content in gas mixtures includes a solid-state electrolyte and two electrodes which are arranged on the solid-state electrolyte, exposed to the gas mixture, and between which a DC voltage can be applied by means of a voltage source, as well as a measuring device for measuring the limiting current flowing between the electrodes as a measure of the oxygen content in the gas mixture. The electrode that functions as the cathode is in contact with the gas mixture without any interposed diffusion barrier. Due to the design of the cathode, the flow of oxygen molecules from the gas mixture to the three-phase boundary between the solid-state electrolyte, the cathode and the gas mixture is limited in a defined manner.

Preferably, the cathode has a low electrochemical activity during the conversion of oxygen molecules to oxygen ions, and the electrode that functions as the anode has a high electrochemical activity during the conversion of oxygen ions to oxygen molecules.

Advantageously, the electrochemical activities of the anode and the cathode differ by a factor of at least 10.

In an advantageous embodiment, the electrodes functioning as the cathode and anode each take the form of a metal-ceramic electrode, with the cathode having a metal content of less than or equal to 50% by weight and the anode having a metal content of greater than or equal to 80% by weight.

Provision may be made for the cathode to have a metal content in the range between 30% by weight and 40% by weight.

As for the ratio of the surface areas of the electrodes, it preferably holds that $$F_K/F_A < 0.7$$

where $F_A$:=surface area of the electrode that functions as the anode
$F_K$:=surface area of the electrode that functions as the cathode Advantageously, the solid-state electrolyte takes the form of a plate-like substrate, and the electrodes functioning as the cathode and anode are disposed in a sub-region on a first side of the substrate.

A heating element may be disposed in a sub-region on the opposite second side of the substrate.

It has proved to be advantageous to design the heating element as a planar, current-traversed resistive heater having an electrical resistance of less than 3.5 Ω at 20° C.

In one possible embodiment, the cathode and the anode are formed as interdigital electrodes on the first side of the substrate.

The metal material in the electrodes may be platinum.

Moreover, the material used for the solid-state electrolyte may be one of the following materials: yttria-stabilized zirconia, scandium-stabilized zirconia, magnesium-stabilized zirconia.

In particular, the solid-state electrolyte may be composed of yttria-stabilized zirconia and have an yttria content in the range between 4 mole percent and 10 mole percent.

Finally, it is possible to provide a coarsely porous protective layer over the surface of the cathode and the anode, which layer does not limit the diffusion at the cathode.

The amperometric gas sensor according to the present invention is advantageous in that the cathode does not need to be provided with a diffusion barrier. The gas sensor can be manufactured using manufacturing methods which would be unsuitable in other cases where a diffusion barrier is needed.

Moreover, it is ensured that the limiting current intended to be measured by a suitable measuring device can be unequivocally associated with the cathode and, in addition, is kinetically limited. This results in a stable; i.e., reproducible limiting current behavior of the amperometric gas sensor of an embodiment of the present invention, even at elevated temperatures; i.e., in the relevant temperature range in which it is operated.

FIG. 1 shows a schematic representation of the amperometric gas sensor according to an embodiment of the present invention.

Solid-state electrolyte F functions as a substrate and has electrodes arranged on one side of the substrate, the electrodes being a cathode K and an anode A between which a DC voltage can be applied by means of a voltage source S. The gas mixture whose oxygen content is to be determined surrounds the two electrodes and solid-state electrolyte F. The electrodes, solid-state electrolyte F and the surrounding gas mixture together form what is known as a three-phase boundary $TPB_K$ and $TPB_A$, respectively, each shown schematically in the figure. At three-phase boundary $TPB_K$ of the cathode, oxygen molecules $O_2$ are ionized and incorporated into vacancies in the lattice of solid-state electrolyte F. When a voltage is applied by voltage source S, a current is caused to flow through the electrodes and solid-state electrolyte F. Charge transfer is via the vacancies in the lattice of solid-state electrolyte F. At three-phase boundary $TPB_A$ of anode A, a reverse reaction takes place and the recombined oxygen molecules $O_2$ are released into the gas mixture. The limiting current flowing between the cathode K and anode A upon application of the DC voltage is measured by the schematically indicated measuring device M, and thus provides a measure of the oxygen content of the gas mixture. Furthermore, a heating element H is disposed on the substrate side opposite the electrodes and used to heat solid-state electrolyte F, since sufficient ionic conductivity sets in only at elevated temperatures.

In the amperometric gas sensor, cathode K and anode A are now in direct contact with the gas mixture surrounding the gas sensor. In particular, in contrast to the known amperometric gas sensors based on the limiting current principle, cathode K is not covered by a diffusion barrier arranged thereabove, but is in direct contact with the gas mixture without any interposed diffusion barrier. In order to reliably limit the flow of oxygen molecules $O_2$ to three-phase boundary $TPB_K$ between solid-state electrolyte F, cathode K and the gas mixture surrounding the gas sensor, as required in the amperometric measurement principle used here, in particular, a specific design of cathode K is decisive in accordance with the present invention. Since no diffusion barrier is provided above cathode K, the present invention provides a different way of limiting the flow of oxygen molecules $O_2$ from the gas mixture to the three-phase boundary $TPB_K$ of cathode K between solid-state electrolyte F, cathode K and the gas mixture. In accordance with the present invention, the required current limitation is now achieved through suitable design of cathode K itself. It is provided, for example, to reduce the length of three-phase boundary $TPB_K$ at cathode K such that cathode K has only a low electrochemical activity during the conversion of oxygen molecules $O_2$ to oxygen ions $O^{2-}$. Therefore, the electrochemical activity of cathode K in this regard is selected to be significantly lower than the electrochemical activity of anode A during the conversion of oxygen ions $O^{2-}$ back to oxygen molecules $O_2$. It is particularly advantageous if the electrochemical activities of cathode K and anode A differ by a factor of at least 10. The activity of the electrodes can be quantitatively determined, for example by measuring device M, as a current between cathode K and anode A that is measured at a predetermined positive or negative voltage. For example, in one exemplary embodiment of the amperometric gas sensor according to the present invention, a current $I_G=30$ μA results at cathode K at a voltage $U_{cathode/anode}=1V$, and a current I=500 μA results at anode A at a voltage $U_{anode/cathode}=-1V$, which means that, here, the electrochemical activities of cathode K and anode A differ by a factor of 16.6.

Due to the now provided combination of an anode A with high electrochemical activity and a cathode K with low electrochemical activity, the diffusion of oxygen molecules $O_2$ toward three-phase boundary $TPB_K$ occurring in cathode K becomes the decisive current-limiting component of the amperometric gas sensor of the present invention. Due to the high activity of anode A, a sufficient amount of oxygen ions $O^{2-}$ can leave the substrate; i.e., solid-state electrolyte F, which means that no further current-limiting and potentially measurement-corrupting effects are produced by other components along the current path.

The current-limiting, kinetically limiting action of cathode K can be accomplished through the selection of suitable materials and material compositions for the electrodes. Specifically, both cathode K and anode A take the form of metal-ceramic electrodes or cermet electrodes. Here, for example, platinum is preferably used as the metal material, and yttria-stabilized zirconia is employed as the ceramic material. Since cathode K and anode A are required to have different electrochemical activities, cathode K is designed to have a metal content of less than or equal to 50% by weight, preferably a metal content between 30% by weight and 40% by weight, whereas anode A, which is required to have a high electrochemical activity, is designed as a metal-ceramic electrode having a metal content of greater than or equal to 80% by weight. With regard to the electrodes, it is also advantageous if the ceramic material and the metal material are intermixed as homogeneously as possible.

Figure 2:
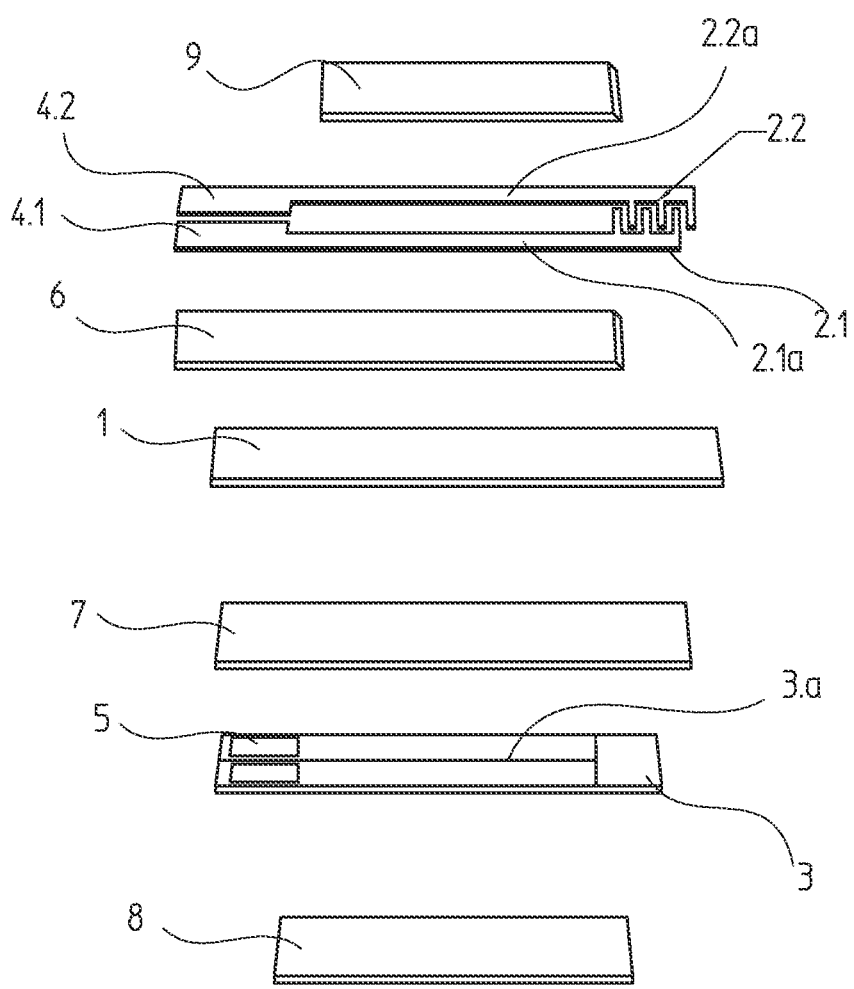
FIG. 2 is an exploded view of an exemplary embodiment of the gas sensor according to the present invention.
Figure 3:
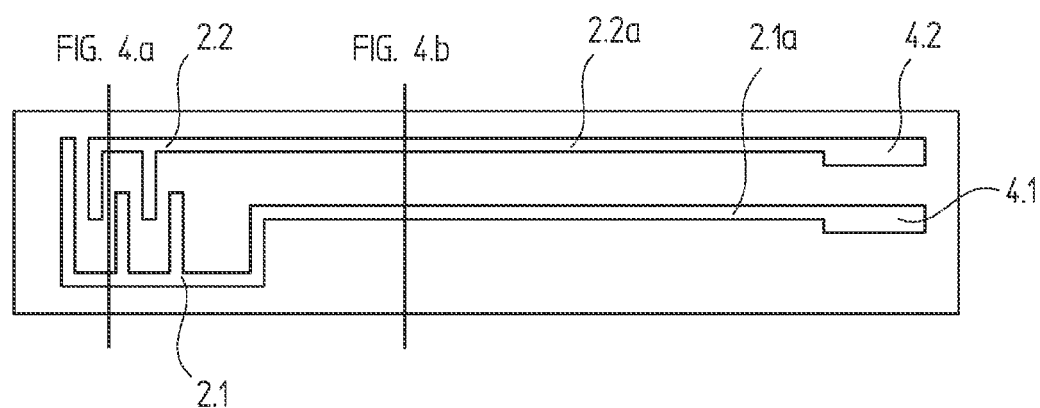
FIG. 3 is a plan view of the exemplary embodiment of the gas sensor according to the present invention.
Figure 4A:
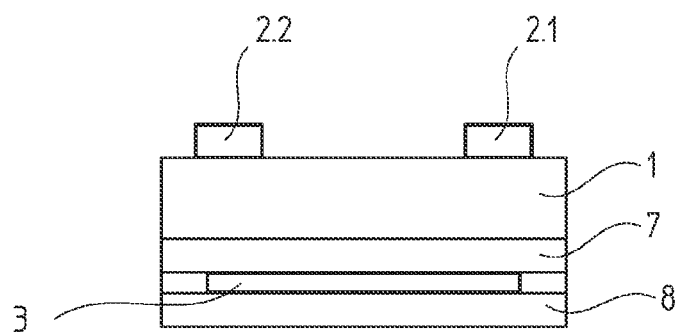
FIGS. 4a, 4b are cross-sectional views of the exemplary embodiment of the gas sensor according to the present invention.
Figure 4B:
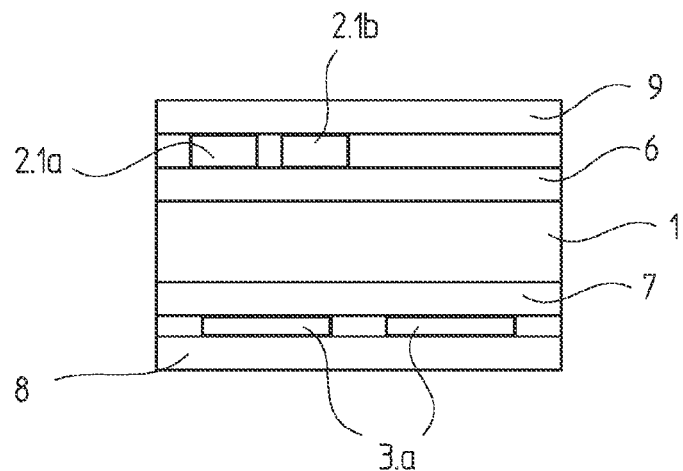

Further measures for optimizing the amperometric gas sensor of the present invention are described below with reference to a specific exemplary embodiment in conjunction with the description of FIGS. 2, 3 4a and 4b. FIG. 2 shows an exploded view of the gas sensor, FIG. 3 shows a plan view, and FIGS. 4a, 4b show cross-sectional views along the planes indicated in FIG. 3.

The amperometric gas sensor according to the present invention includes a solid-state electrolyte 1 on which are arranged two electrodes in the form of an anode 2.1 and a cathode 2.2. Solid-state electrolyte 1 takes the form of a plate-like substrate of rectangular cross section. The material selected for solid-state electrolyte 1 is one having a sufficiently high conductivity for the oxygen ions formed at the three-phase boundary of cathode 2.2. In a preferred variant, yttria-stabilized zirconia having an yttria content between 4 mole percent and 10 mole percent is used.

In the illustrated exemplary embodiment of the amperometric gas sensor, anode 2.1 and cathode 2.2 are disposed only in a sub-region on a first side (top side) of the substrate. In FIG. 2, this sub-region is located at the right edge, while in FIG. 3, this sub-region is located at the left edge. Anode 2.1 and cathode 2.2 are configured as interleaved interdigital electrodes in this sub-region. Via conductors 2.1a, 2.1b, anode 2.1 and cathode 2.2 are connected to contact regions 4.1, 4.2 which are located at the opposite longitudinal end of the substrate and via which anode 2.1 and cathode 2.2 can be electrically contacted. As can be seen in the cross-sectional view of FIG. 4b, both conductors 2.1a, 2.1b and contact regions 4.1, 4.2 are not arranged directly on solid-state electrolyte 1, but on an insulating layer 6 provided between solid-state electrolyte 1 and conductors 2.1a, 2.1b and, respectively, contact regions 4.1, 4.2. It is advantageous for insulating layer 6 to be of a material which is neither electrically nor ionically conductive. Further, the material of insulating layer 6 should have good adherence to the adjacent materials and should be selected such that its thermal expansion coefficient matches, as close as possible, that of the material of solid-state electrolyte 1.

Moreover, a protective layer 9 is disposed above conductors 2.1a, 2.1b on the first side of the substrate outside the sub-region containing anode 2.1 and cathode 2.2. Furthermore, as can be seen, for example, from FIG. 2, protective layer 9 does not cover the edge area of the substrate where contact regions 4.1, 4.2 are located. With regard to suitable materials for protective layer 9, substantially the same requirements apply as in the case of the material for insulating layer 6.

As can be seen in particular in the cross-sectional view of FIGS. 4a and 4b, the electrodes; i.e., anode 2.1 and cathode 2.2., are in direct contact with the gas mixture which surrounds the gas sensor and whose oxygen content is to be determined by the gas sensor of the present invention. In particular, as mentioned earlier, cathode 2.2 is not covered by a diffusion barrier arranged thereabove, but is in direct contact with the gas mixture without any interposed diffusion barrier. In order to reliably limit the flow of oxygen molecules to the three-phase boundary between solid-state electrolyte 1, cathode 2.2 and the gas mixture surrounding the gas sensor in the amperometric measurement principle used here, cathode 2.2 is designed as discussed above.

On a second side (bottom side) of the substrate, a heating element 3 is disposed in a sub-region opposite the sub-region containing the electrodes; i.e., anode 2.1 and cathode 2.2, on the first side of the substrate. Via heating element 3, the sub-region of solid-state electrolyte 1 in which the electrodes are located can be heated to the required operating temperature in the range between 700° C.-800° C. Heating element 3 is designed as a current-traversed resistive heater having planar metal tracks. It is particularly advantageous for the gas sensor according to the present invention if heating element 3 is designed to have an electrical resistance below 3.5 Ω at 20° C. This makes it possible to substantially prevent potential crosstalk of the heating element voltage to the electrodes on the other side of the substrate. Such crosstalk would result in an unstable current-voltage characteristic, and thus in measurement errors during the determination of the oxygen content in the gas mixture.

Suitable materials for the metal tracks of heating element 3 include platinum (deposited, for example, as a screen printed platinum paste), molybdenum and tungsten. Here, too, it is generally advantageous if the material used for heating element 3 is selected to match the thermal properties of solid-state electrolyte 1. Heating element 3, which is disposed at a longitudinal end of solid-state electrolyte 1, is connected via conductors 3.a to contact regions 5 at the opposite longitudinal end of the substrate, and may be connected via contact regions 5 to a power source.

In the exemplary embodiment shown, the metal tracks of heating element 3 are not arranged directly on the substrate or solid-state electrolyte 1, but on another insulating layer 7, which is here disposed over the entire surface of the second side of the substrate. With regard to the material of this insulating layer 7, the same requirements apply as in the case of the above-mentioned insulating layer 6. A protective layer 8 is provided over the metal tracks of the resistive heater on the second side of the substrate except for contact regions 5. The requirements discussed earlier herein apply also to this protective layer 8.

Since, as mentioned earlier, no diffusion barrier is provided above cathode 2.2, the present invention provides a different way of limiting the flow of oxygen molecules from the gas mixture to the three-phase boundary between solid-state electrolyte 1, cathode 2.2 and the gas mixture. As discussed above, the required current limitation is achieved through suitable design of cathode 2.2 itself As a further measure to selectively adjust a different electrochemical activity ratio between cathode 2.2 and anode 2.1 in the amperometric gas sensor of the present invention, provision may be made to suitably size the surface areas of the electrodes. Once a specific electrode activity is adjusted in a defined manner via the respective metal/ceramic ratio, and given a constant exchange current density, the electrode current can be increased or reduced as required by changing the electrode surface area. In this connection, it is particularly advantageous if for the ratio of the surface area $F_K$ of cathode 2.2 to the surface area $F_A$ of anode 2.1 on solid-state electrolyte 1, it holds that $$F_K/F_A < 0.7$$

i.e., that the ratio of the surface area $F_K$ of cathode 2.2 to the surface area $F_A$ of anode 2.1 on solid-state electrolyte 1 should preferably be selected to be less than 0.7, where
$F_A$:=surface area of the electrode that functions as the anode
$F_K$:=surface area of the electrode that functions as the cathode In addition to the exemplary embodiment described herein, other embodiments are of course possible within the scope of the present invention.

For example, as an alternative to the above-mentioned yttria-stabilized zirconia, magnesium-stabilized zirconia or scandium-stabilized zirconia could be used as the material for the solid-state electrolyte.

Instead of the interdigital electrode pattern provided in the exemplary embodiment, a different geometry could be used for the cathode and anode. For example, radially symmetric or U-shaped electrode geometries would be conceivable.

Furthermore, in order to protect the gas sensor of the present invention from impacting water droplets, a coarsely porous protective layer may be provided over the surface of the cathode and the anode. It should be noted that such a coarsely porous protective layer does not limit the diffusion at the cathode. I.e., even in such an embodiment, the cathode is in contact with the gas mixture without any interposed diffusion barrier.

Instead of arranging the two electrodes together on one side of the solid-state electrolyte, it is possible to dispose the cathode and the anode on opposite sides of the substrate. In this case, no separate heating element is provided in the gas sensor, but the gas sensor is used in an environment which has a sufficiently high constant temperature T >700° C.

Finally, instead of building up the gas sensor of the present invention on a pre-baked substrate, it may be formed as a sandwich structure using so-called "green tapes", etc.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. An amperometric gas sensor for determining oxygen content in a gas mixture, comprising:
   a solid-state electrolyte;
   a first electrode configured as a cathode and a second electrode configured as an anode disposed on the solid-state electrolyte and exposed to the gas mixture, the cathode being in contact with the gas mixture without any interposed diffusion barrier and having a design such that a flow of oxygen molecules from the gas mixture to a three-phase boundary between the solid-state electrolyte, the cathode and the gas mixture is limited in a defined manner, wherein the cathode is configured to have a low electrochemical activity during conversion of oxygen molecules to oxygen ions and the anode is configured to have a high electrochemical activity during conversion of oxygen ions to oxygen molecules, and wherein the electrochemical activities of the anode and the cathode differ by a factor of at least 10;
   a voltage source configured to apply a DC voltage between the electrodes; and
   a measuring device configured to measure a limiting current flowing between the electrodes as a measure of the oxygen content in the gas mixture.

2. The amperometric gas sensor as recited in claim 1, wherein the electrodes are metal-ceramic electrodes, the first electrode having a metal content of less than or equal to 50% by weight and the second electrode having a metal content of greater than or equal to 80% by weight.

3. The amperometric gas sensor as recited in claim 2, wherein the first electrode has a metal content in a range between 30% by weight and 40% by weight.

4. The amperometric gas sensor as recited in claim 1, wherein a ratio of surface areas of the electrodes is as follows $$F_K/F_A < 0.7$$

where
$F_A$ is the surface area of the second electrode, and
$F_K$ is the surface area of the first electrode.

5. The amperometric gas sensor as recited in claim 1, wherein the solid-state electrolyte is a plate-like substrate, and the electrodes are disposed in a sub-region on a first side of the substrate.

6. The amperometric gas sensor as recited in claim 5, further comprising a heating element disposed in a sub-region on a second side of the substrate opposite the first side.

7. The amperometric gas sensor as recited in claim 6, wherein the heating element is a planar, current-traversed resistive heater having an electrical resistance of less than 3.5 Ω at 20° C.

8. The amperometric gas sensor as recited in claim 5, wherein the electrodes are interdigital electrodes on the first side of the substrate.

9. The amperometric gas sensor as recited in claim 1, wherein each of the electrodes includes platinum as a metal material.

10. The amperometric gas sensor as recited in claim 1, wherein a material forming the solid-state electrolyte is one of yttria-stabilized zirconia, scandium-stabilized zirconia and magnesium-stabilized zirconia.

11. The amperometric gas sensor as recited in claim 10, wherein the solid-state electrolyte is composed of yttria-stabilized zirconia and has an yttria content in the range between 4 mole percent and 10 mole percent.

12. The amperometric gas sensor as recited in claim 1, further comprising a coarsely porous protective layer disposed over the surfaces of the electrodes, the protective layer being configured so as to not limit diffusion at the cathode.

* * * * *